US011318239B2

(12) United States Patent
Ali et al.

(10) Patent No.: US 11,318,239 B2
(45) Date of Patent: May 3, 2022

(54) SYSTEMS AND METHODS FOR PERFORMING ONLINE EXTRACORPOREAL PHOTOPHERESIS

(71) Applicant: Fenwal, Inc., Lake Zurich, IL (US)

(72) Inventors: Zahra R. Ali, Chicago, IL (US); Lan T. Nguyen, Vernon Hills, IL (US); Katherine N. Radwanski, Highland Park, IL (US); Angela N. Carlson, Arlington Heights, IL (US); Tanima J. Abedin, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 580 days.

(21) Appl. No.: 16/286,726

(22) Filed: Feb. 27, 2019

(65) Prior Publication Data
US 2019/0269844 A1  Sep. 5, 2019

Related U.S. Application Data

(60) Provisional application No. 62/636,927, filed on Mar. 1, 2018.

(51) Int. Cl.
*A61M 1/36* (2006.01)
*A61M 1/30* (2006.01)
*A61M 1/34* (2006.01)

(52) U.S. Cl.
CPC ............ *A61M 1/3683* (2014.02); *A61M 1/30* (2013.01); *A61M 1/3455* (2013.01);
(Continued)

(58) Field of Classification Search
CPC .... A61M 1/30; A61M 1/3455; A61M 1/3496; A61M 1/3683; A61M 1/3692;
(Continued)

(56) References Cited

U.S. PATENT DOCUMENTS

| 5,360,542 A | 11/1994 | Williamson, IV et al. |
| 5,984,887 A | 11/1999 | McLaughlin et al. |

(Continued)

FOREIGN PATENT DOCUMENTS

| EP | 3053616 A1 | 8/2016 |
| EP | 3132817 A1 | 2/2017 |

OTHER PUBLICATIONS

"Therakos CellEx Photopheresis System", Operator's Manual, Rev. 4.0-1460451, 1470056A_TB#20_EN-CA, Oct. 2014, 382 pages.
(Continued)

*Primary Examiner* — Benjamin J Klein
(74) *Attorney, Agent, or Firm* — Cook Alex Ltd.

(57) ABSTRACT

Systems and methods for performing online extracorporeal photopheresis of mononuclear cells are disclosed. During a mononuclear cell collection cycle, blood is removed from a source and separated into a plasma constituent, a mononuclear cell-containing layer, and red blood cells, followed by the collection of a pre-product including at least a portion of the mononuclear cell-containing layer and at least a portion of the separated red blood cells. The mononuclear cell collection cycle may be repeated, followed by the production of a single mononuclear cell product using the collected pre-product(s). The mononuclear cell product is irradiated using a fixed dose of light, such that the mononuclear cell product is produced so as to have a predetermined volume and a predetermined hematocrit, regardless of the number of pre-products used to produce the mononuclear cell product. Following irradiation, at least a portion of the irradiated mononuclear cell product is returned to the source.

20 Claims, 5 Drawing Sheets

(52) U.S. Cl.
CPC ........ *A61M 1/3496* (2013.01); *A61M 1/3692* (2014.02); *A61M 1/3693* (2013.01); *A61M 1/3696* (2014.02); *A61M 2202/0021* (2013.01); *A61M 2202/0429* (2013.01); *A61M 2202/0443* (2013.01); *A61M 2205/053* (2013.01); *A61M 2205/3306* (2013.01)

(58) Field of Classification Search
CPC .............. A61M 1/3693; A61M 1/3696; A61M 2202/0021; A61M 2202/0429; A61M 2202/0443; A61M 2205/053; A61M 2205/3306
See application file for complete search history.

(56) References Cited

U.S. PATENT DOCUMENTS

| | | | |
|---|---|---|---|
| 6,027,657 A | 2/2000 | Min et al. | |
| 7,433,030 B2 | 10/2008 | Waldo et al. | |
| 9,399,093 B2 | 7/2016 | Min et al. | |
| 2004/0127841 A1* | 7/2004 | Briggs | A61M 1/3681 604/6.01 |
| 2013/0197419 A1* | 8/2013 | Min | B04B 11/02 604/6.01 |
| 2015/0196706 A1 | 7/2015 | Radwanski et al. | |
| 2015/0359959 A1* | 12/2015 | Radwanski | A61M 1/3693 210/748.11 |
| 2016/0195555 A1 | 7/2016 | Wegener et al. | |
| 2017/0319775 A1 | 11/2017 | Min et al. | |

OTHER PUBLICATIONS

Extended European Search Report for European Patent Application No. EP19159588.3, dated Jul. 29, 2019, 8 pages total.

* cited by examiner

SYSTEMS AND METHODS FOR PERFORMING ONLINE EXTRACORPOREAL PHOTOPHERESIS

CROSS-REFERENCE TO RELATED APPLICATIONS

This application claims the benefit of and priority of U.S. Provisional Patent Application Ser. No. 62/636,927, filed Mar. 1, 2018, the contents of which are incorporated by reference herein.

BACKGROUND

Field of the Disclosure

The present disclosure relates to extracorporeal photopheresis ("ECP"). More particularly, the present disclosure is directed to ensuring that a mononuclear cell product having a consistent volume and composition is collected in view of variable input parameters.

Description of Related Art

Whole blood is made up of various cellular and non-cellular components such as red cells, white cells, and platelets suspended in its liquid component, plasma. Whole blood can be separated into its constituent components (cellular, liquid, or other), with one or more of the separated components being administered to a patient in need of that particular component or components.

The administration of blood and/or blood components is common in the treatment of patients suffering from disease. Rather than infuse whole blood, it is more typical for individual components to be administered to the patient(s) as their needs require. For example, administration (infusion) of platelets is often prescribed for cancer patients whose ability to make platelets has been compromised by chemotherapy. Infusion of white blood cells (i.e., mononuclear cells or "MNCs"), after the cells have undergone some additional processing or treatment, may also be prescribed for therapeutic reasons, including treatment of diseases that specifically involve the white blood cells. Thus, it is often desirable to separate and collect the desired blood component from whole blood and then treat the patient with the specific blood component. The remaining components may be returned to the donor, discarded, or retained for other uses.

There are several diseases or disorders which are believed to primarily involve mononuclear cells, such as cutaneous T-cell lymphoma, organ allograft rejection after transplantation and autoimmune diseases such as rheumatoid arthritis, systemic sclerosis, among others.

Cutaneous T-cell lymphoma ("CTCL") is a term that is used to describe a wide variety of disorders. Generally, CTCL is a type of cancer of the immune system where T-cells (a type of mononuclear cell) mutate or grow in an uncontrolled way, migrate to the skin, and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility, and hair loss.

Organ allograft rejection may be characterized as the rejection of tissues that are foreign to a host, including transplanted cardiac tissue as well as lung, liver, and renal transplants. Immunosuppression drug therapy following transplantation is common. However, there are potential drawbacks including reoccurring infection due to the compromised competence of the immune system caused by this type of therapy.

Similarly, graft versus host disease ("GVHD") is a complication that can occur after a stem cell or bone marrow transplant, in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient is usually administered a drug that suppresses the immune system, which helps reduce the chances or severity of GVHD.

Autoimmune diseases, including rheumatoid arthritis ("RA") and progressive systemic sclerosis ("PSS"), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to, among other things, joint destruction in RA and inflammation of the connective tissue in PSS.

Where existing therapies for treating one or more diseases may result in certain unintended side effects, additional treatment may be desired or required. One known procedure which has been shown to be effective in the treatment of diseases and/or the side effects of existing therapies involving mononuclear cells is ECP. ECP (which is also sometimes referred to as extracorporeal photochemotherapy) is a process that includes: (1) collection of MNCs from a patient, (2) photoactivation treatment of the collected MNCs, and (3) reinfusion of the treated MNCs back to the patient. More specifically, ECP involves the extracorporeal exposure of peripheral blood mononuclear cells combined with a photoactive compound, such as 8-methoxypsoralen or "8-MOP," which is then photoactivated by ultraviolet ("UV") light, followed by the reinfusion of the treated MNCs. It is believed that the combination of 8-MOP and UV radiation causes apoptosis or programmed cell death of ECP-treated T-cells.

While the clinical benefits of ECP have been recognized, the use of ECP is not without its own drawbacks, including the systems and methods by which the ECP treatment is performed. For example, there are currently two commonly used methods for performing photopheresis—online and offline methods. Systems for performing online ECP include, for example, the CELLEX® and UVAR XTS® systems available from Therakos, Inc., of Exton, Pa. In online methods, a dedicated photopheresis device is used to perform the entire therapy, including reinfusion of treated MNCs. Such devices are "dedicated" photopheresis devices, designed only for performing photopheresis and cannot perform other collection protocols needed in a hospital or blood processing setting including, for example, multifunctional apheresis protocols for collection of platelets, plasma, red blood cells ("RBCs"), granulocytes, and/or perform plasma/RBC exchange protocols. In offline photopheresis methods, a multifunctional apheresis device may be used to collect MNCs. The collected MNCs, typically contained in one or more collection containers, are severed or otherwise separated from the tubing set used during collection, where they are later treated in a separate irradiation or UVA light device, followed by manual reinfusion of the treated cells to a patient. However, during such offline methods, when the cells are transferred from the apheresis device to the irradiation device (which device may be located in another room or laboratory) communication with the patient must be severed and accordingly, the cells detached from the patient. Thus, additional traceability procedures are required to insure that the treated MNC product is ultimately reinfused into the correct patient.

In response to the foregoing shortcomings, an online ECP system capable of performing other collection protocols has been proposed, as described in U.S. Pat. No. 9,399,093, which is hereby incorporated herein. In addition to being able to perform other collection protocols (by providing the combination of a multifunctional automated apheresis device and a separate irradiation device), an additional advantage of this system is its ability to process larger volumes of whole blood during a procedure compared to conventional online ECP systems.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, the present disclosure is directed to an extracorporeal photopheresis system comprising a separation device configured to execute a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product. The separation device is further configured to produce a single mononuclear cell product from said pre-product, which is irradiated with a fixed dose of light by an irradiation device of the system. The system further includes a controller configured to control operation of at least the separation device, which controller is further configured to allow for execution of one or more of the mononuclear cell collection cycles prior to production of the single mononuclear cell product, with the single mononuclear cell product being produced using the pre-products collected during each mononuclear cell collection cycle. The controller controls the separation device to produce the mononuclear cell product with a predetermined volume and a predetermined hematocrit, regardless of the number of mononuclear cell collection cycles executed and the number of pre-products used to produce the mononuclear cell product.

In another aspect, the present disclosure is directed to a method for extracorporeal photopheresis, which includes executing a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product. The mononuclear cell collection cycle is optionally repeated, with a single mononuclear cell product being produced using the pre-products collected during each mononuclear cell collection cycle. The mononuclear cell product is irradiated using a fixed dose of light, with at least a portion of the irradiated mononuclear cell product being returned to the blood source. The mononuclear cell product has a predetermined volume and a predetermined hematocrit regardless of the number of mononuclear cell collection cycles executed and the number of pre-products used to produce the mononuclear cell product.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
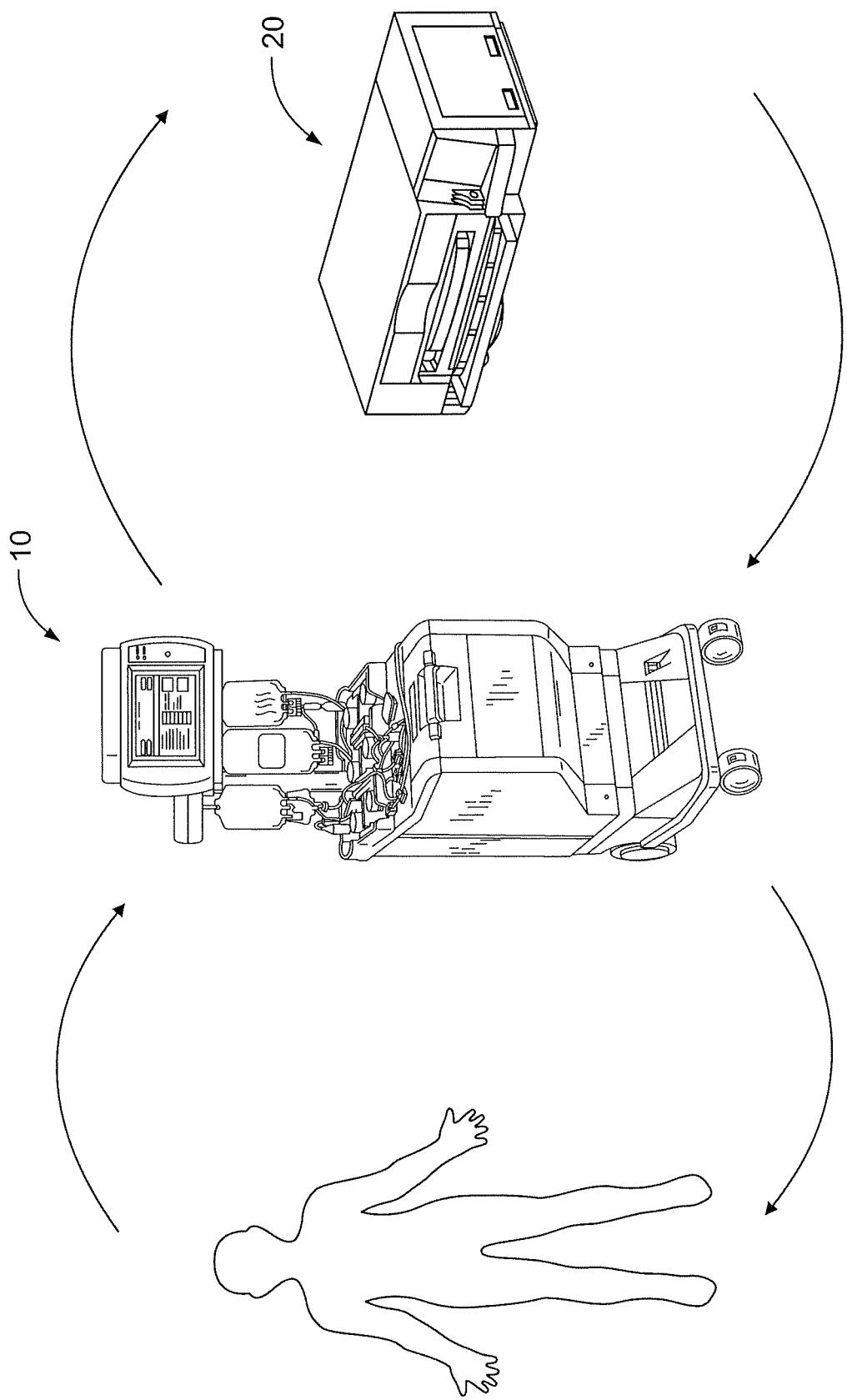
FIG. 1 is a diagram showing the durable components of an online ECP system according to an aspect of the present disclosure.

The subject matter of the present disclosure relates generally to systems and methods for performing online ECP treatment as described in U.S. Pat. No. 9,399,093. FIG. 1 shows, in general, exemplary mechanical components that may make up the system and be used in the methods described herein. In accordance with the present disclosure, the system includes a separation device 10 and a treatment (i.e., irradiation) device 20. In the illustrate embodiment, the irradiation device 20 is independent and housed separately from the separation device 10. Although separately provided, it is advantageous for the separation device 10 and the irradiation device 20 to be located adjacent to each other. For example, the separation device 10 and the irradiation device 20 may be located in the same room, but physically spaced several feet or yards from each other. The irradiation device 20 may be on a table top located near or adjacent to the separation device 10, allowing an operator or clinician to have access to both devices during an ECP procedure. Systems according to the present disclosure may include additional devices, such as a washing device (which may be incorporated into the separation device 10) without departing from the scope of the present disclosure.

A disposable fluid flow circuit or fluid processing assembly 200 (FIGS. 2 and 4) provides a sterile closed pathway between the patient, the separation device 10, and the irradiation device 20. With reference to FIG. 1, whole blood is drawn into the fluid circuit 200 from the patient and introduced into the separation device 10, with MNCs being separated from other blood components. Other components separated from the whole blood, such as red blood cells and platelets may be returned to the patient or collected in pre-attached containers of the fluid circuit 200.

The collected MNC product is then treated in the irradiation device 20, which involves the photoactivation of a photoactive agent that has been combined with the MNCs. Once treated, the MNC product may optionally be provided to a washing device, which, as noted above, may be incorporated into the separation device 10 and, preferably, is one and the same. If the treated MNC product is to be washed, it is suspended in a wash solution within the separation/washing device 10. The suspension of MNCs in the wash solution is then subjected to a centrifugal field (or other environment which can effect separation of the fluid components), whereby the MNCs are concentrated and separated from the supernatant, which typically includes excess and unbound photoactivation agent. The concentrated MNCs are finally returned to the patient, with the supernatant being diverted to an appropriate waste container.

Devices useful in the collection (and washing) of MNCs include the device currently marketed as the AMICUS® separator by Fenwal, Inc., of Lake Zurich, Ill., which is an affiliate of Fresenius Kabi AG of Bad Homburg, Germany. MNC collections using a device of this type are described in greater detail in U.S. Pat. No. 6,027,657, which is hereby incorporated herein by reference. Preferably, the apparatus used for the harvesting, collection, and reinfusion of MNCs in accordance with the systems and methods described herein is a multifunctional automated apheresis device, as is the case with the AMICUS® separator. In other words, it is preferable that the separation device 10 be a multifunctional automated apparatus that can perform various collection protocols and/or serve multiple purposes, as may be needed by a particular hospital or facility, such that it can be used not only in performing ECP procedures of the type described herein, but can also be used for other purposes including the collection of blood and blood components including platelets, plasma, red blood cells, and granulocytes and/or the performance of plasma/RBC exchange, among other functions that may be required by the hospital or medical facility.

Devices useful in the irradiation of collected MNCs include those available from sources such as Cerus Corporation, of Concord, Calif. One example of a suitable irradiation device is described in U.S. Pat. No. 7,433,030, which is hereby incorporated herein by reference.

Figure 2:
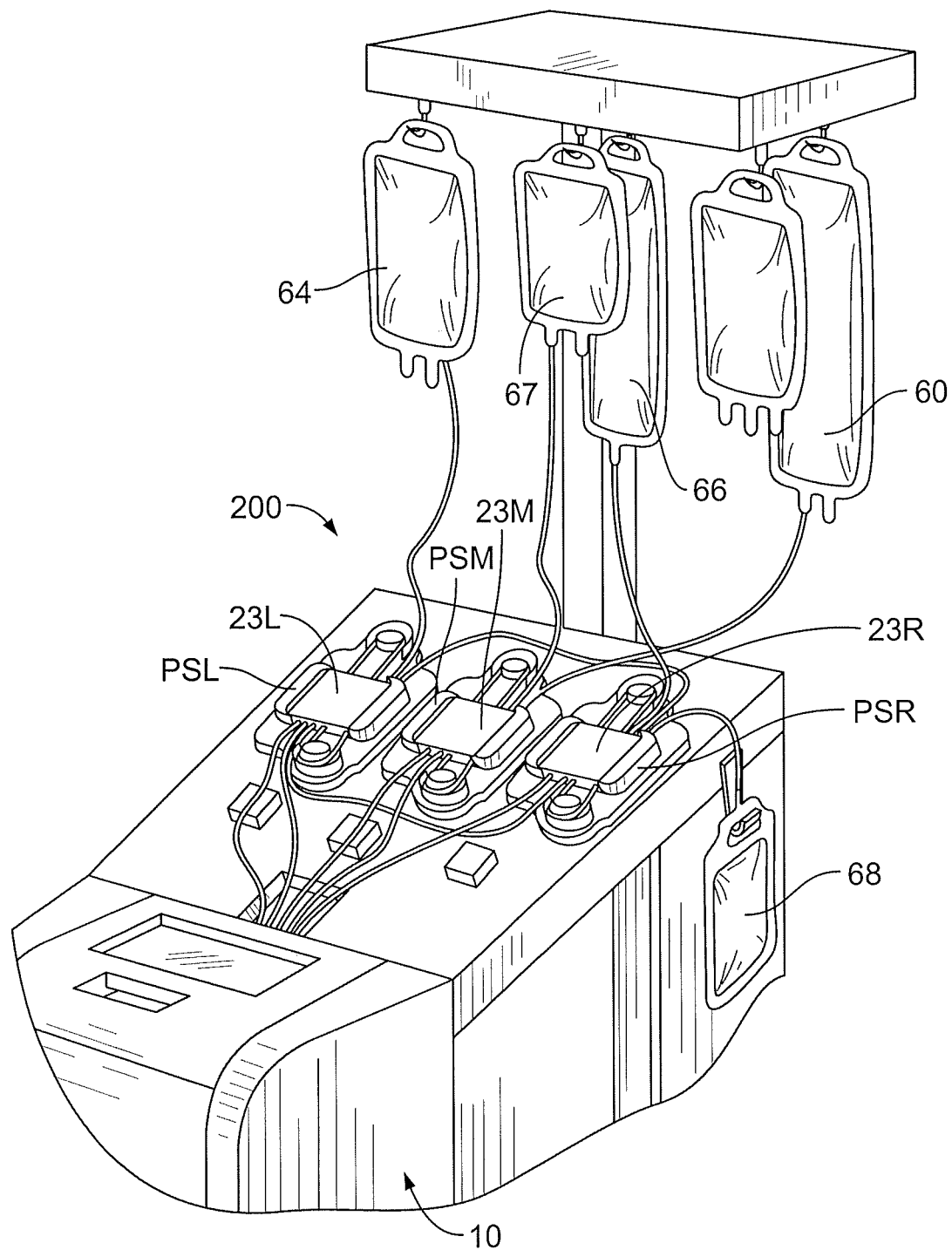
FIG. 2 is a partial perspective view of a multifunctional apheresis separator of the ECP system of FIG. 1.
Figure 3:
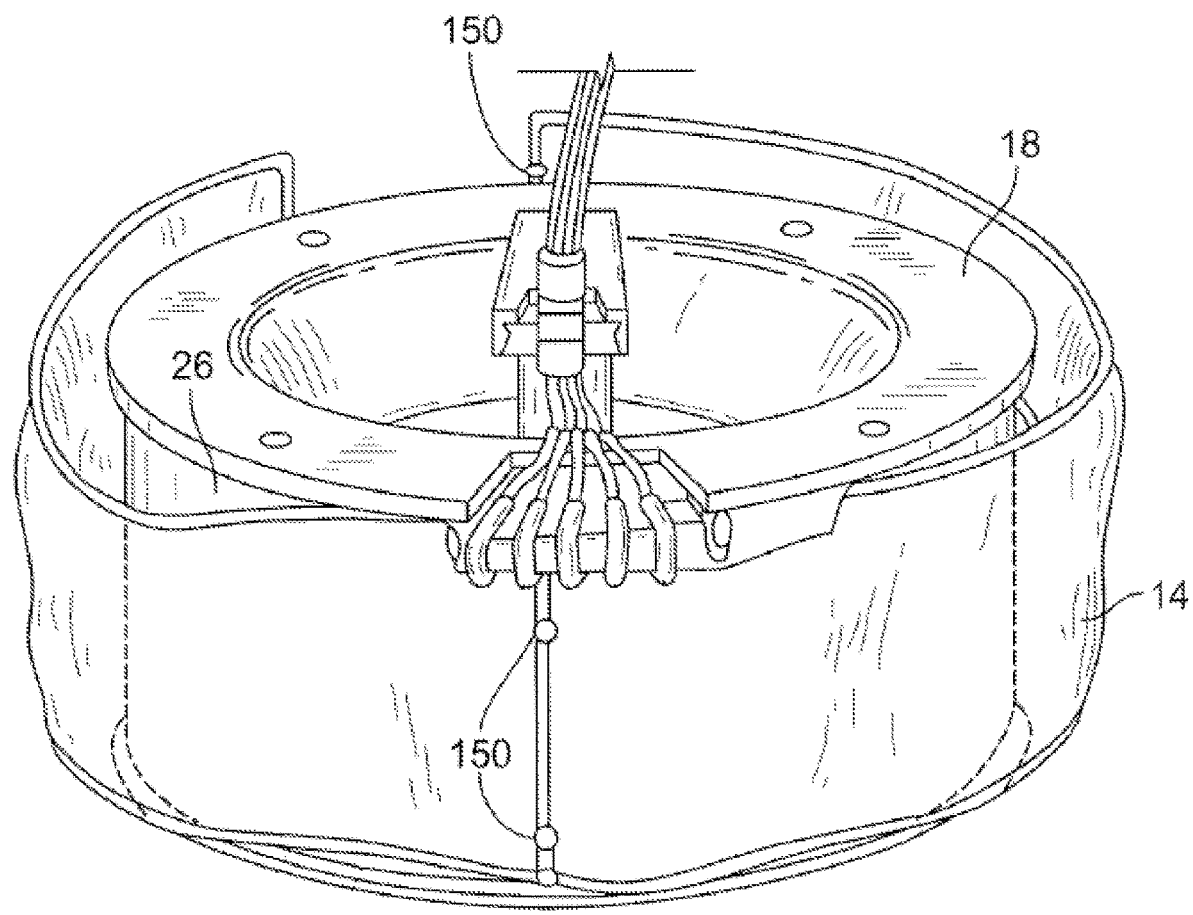
FIG. 3 is a perspective view of a separation chamber of a disposable fluid flow circuit used with the separator of FIG. 2.
Figure 4:
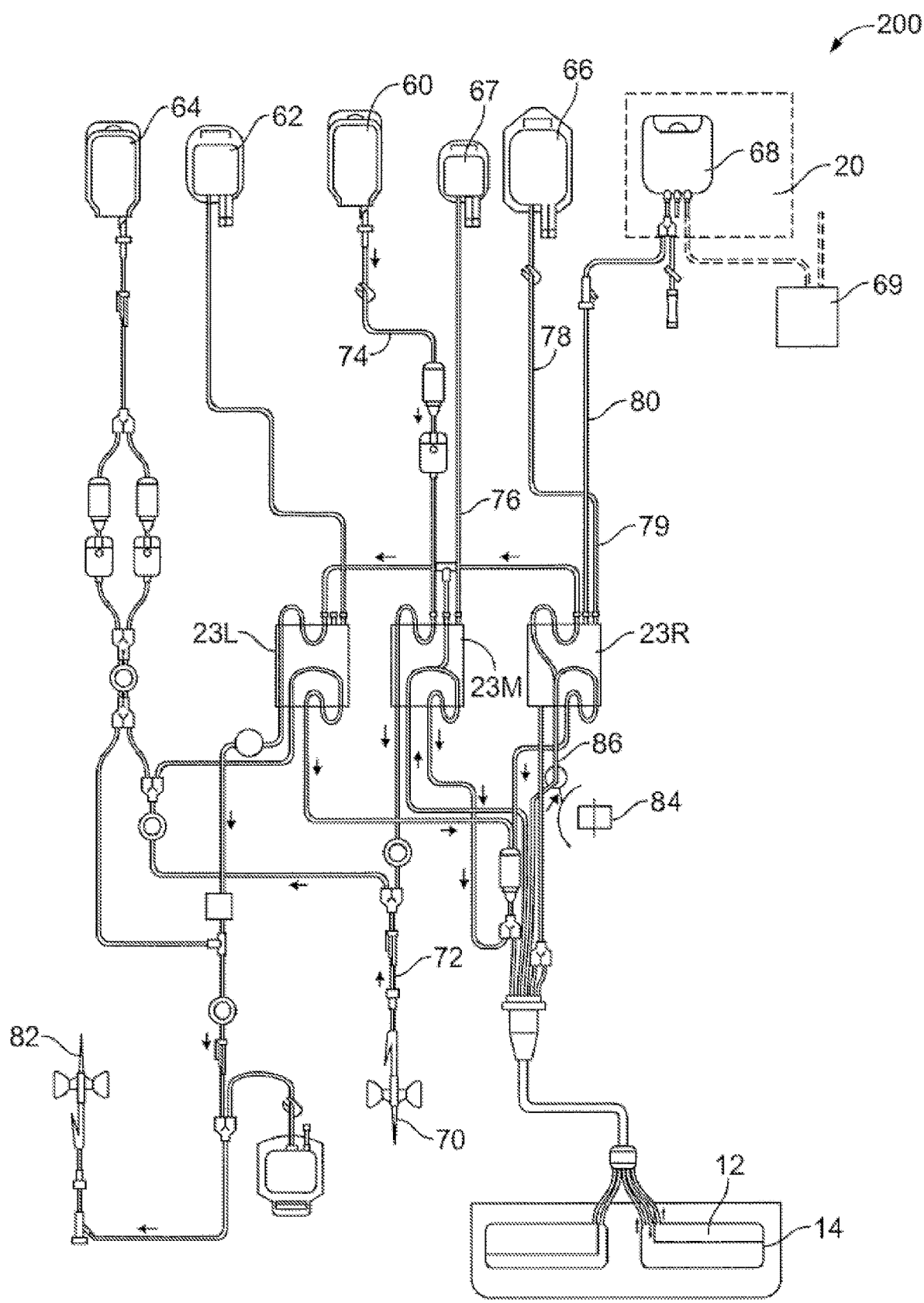
FIG. 4 is a diagram of the fluid flow circuit used in combination with the separator of FIG. 2.

FIG. 2 more particularly shows an exemplary fluid circuit or fluid processing assembly 200 mounted to a front panel of the separation device 10, with FIG. 3 showing a separation chamber 14 of the fluid circuit 200 and FIG. 4 showing the entire fluid circuit 200. The fluid circuit 200 includes a plurality of processing cassettes 23L, 23M and 23R with tubing loops for association with peristaltic pumps of pump stations PSL, PSM, and PSR (respectively) of the separation device 10 (FIG. 2). The fluid circuit 200 also includes a network of tubing and pre-connected containers for establishing flow communication with the patient and for processing and collecting fluids and blood and blood components, as best shown in FIG. 4. As shown in FIGS. 2 and 4, the fluid circuit 200 may include an anticoagulant container 60, a waste container 62 for collecting waste from one or more steps in the ECP procedure, a container 64 for holding saline or other wash or resuspension medium, a plasma collection container 66, an RBC collection container 67, an MNC collection container 68, and, optionally, a container 69 for holding the photoactivation agent.

While FIG. 2 shows the MNC collection container 68 hanging from the side of the separation device 10, it may instead be housed within the irradiation device 20 (represented in FIG. 4 by broken lines), thereby eliminating the step of having the operator place the MNC collection container 68 into the irradiation device 20. It will, thus, be appreciated that the tubing leading to and/or from the MNC collection container 68 in the fluid circuit 200 is preferably of a sufficient length to reach the irradiation device 20 which, as noted above, is preferably positioned adjacent to the separation device 10. Such a configuration is advantageous to the extent that the MNC collection container 68 does not have to be separated or otherwise disconnected from the fluid circuit 200 for the collected MNCs to be treated in the irradiation device 20.

As shown in FIG. 4, the fluid circuit 200 further includes an inlet line 72, an anticoagulant line 74 connected to the anticoagulant container 60, an RBC line 76 extending between the RBC collection container 67 and a port of the middle cassette 23M for conveying separated red blood cells from a first stage 12 of the separation chamber 14 into the RBC collection container 67, a plasma line 78 for conveying separated plasma to the plasma collection container 66, and an MNC line 80 for conveying separated MNCs to and from the first stage 12 of the separation chamber 14 (via the right cassette 23R). As will be known to those of skill in the art, the fluid circuit 200 also includes at least one access device (e.g., a venipuncture needle) for accessing the circulatory system of the patient. In the embodiment of FIG. 4, the fluid circuit 200 includes an inlet needle 70 and a return needle 82, while in other embodiments, a single needle can serve as both the inlet and outlet needle. Fluid flow through the fluid circuit 200 is preferably driven, controlled, and adjusted by a microprocessor-based controller of the separation device 10, which controls operation of the various valves, pumps, weight scales, and sensors of the separation device 10, as described in greater detail in U.S. Pat. No. 6,027,657.

A centrifuge of the separation device 10 includes a rotating spool element 18 (FIG. 3) and a concentric, outer bowl element (not shown), with the separation chamber 14 positioned within an annular gap defined by the spool element 18 and the bowl element. The bowl element and the spool element 18 are pivoted on a yoke (not illustrated) between an upright position and a suspended position. When upright, the bowl element and the spool element 18 are presented for access by the user. A mechanism permits the spool element 18 and the bowl element to be opened so that the user can wrap the separation chamber 14 about the spool element 18, as in FIG. 3. Pins 150 on the spool element 18 engage cutouts on the separation chamber 14 to secure the separation chamber 14 on the spool element 18. With the separation chamber 14 so loaded into the centrifuge, yoke is adjusted to pivot the spool element 18 and the bowl element into their suspended position for rotation about a rotational axis to create a centrifugal field within the separation chamber 14.

The radial boundaries of the centrifugal field are formed by the interior wall of the bowl element and the exterior wall 26 of the spool element 18. The interior bowl wall defines the high-G wall. The exterior spool wall 26 defines the low-G wall. Further details of the mechanism for causing relative movement of the spool element 18 and the bowl element as just described are disclosed in U.S. Pat. No. 5,360,542, which is hereby incorporated herein by reference.

Figure 5:
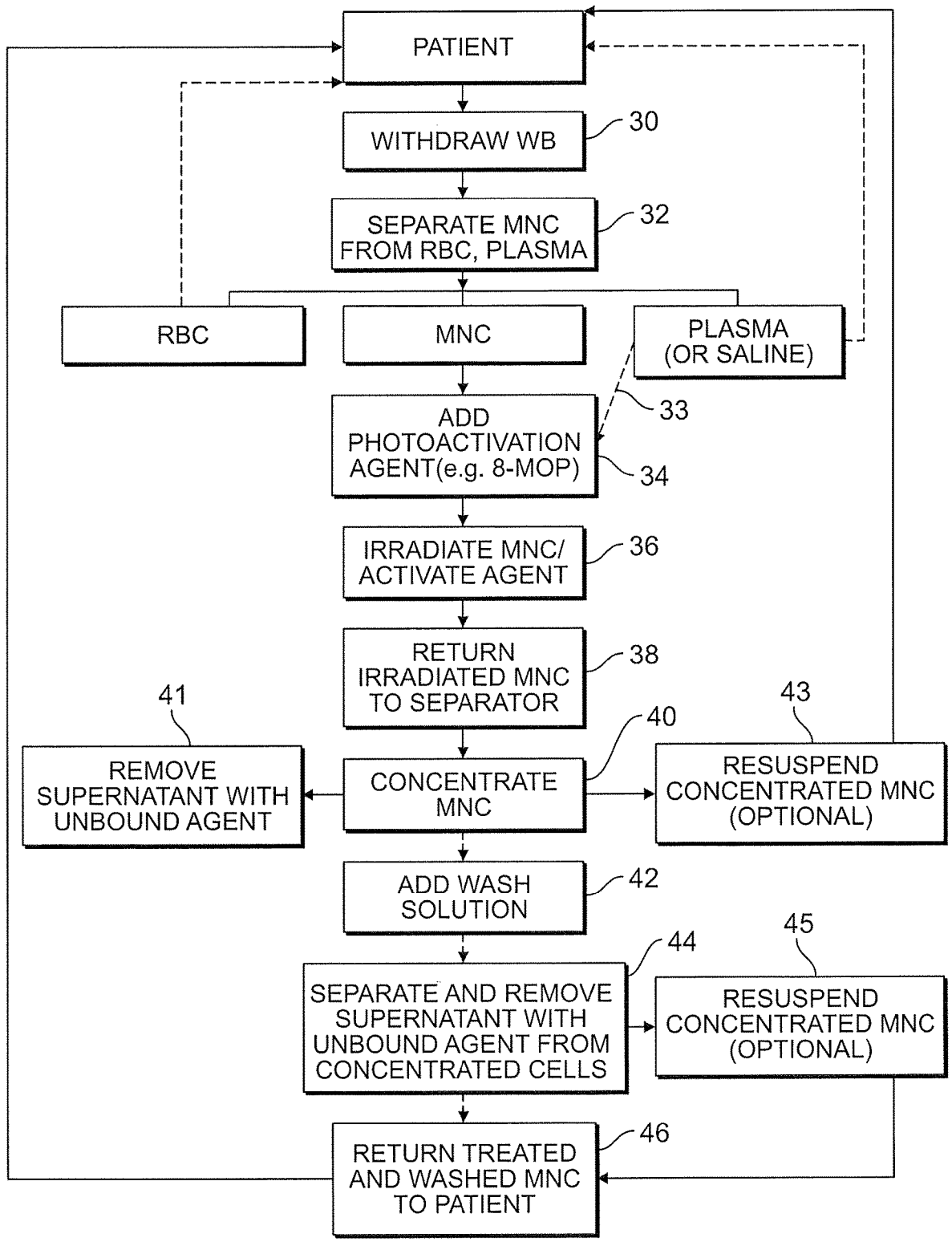
FIG. 5 is a flow chart setting forth the steps of the method of an exemplary ECP procedure.

Turning now to the method of treating MNCs, FIG. 5 shows the various steps of an exemplary procedure according to an aspect of the present disclosure. As shown in FIG. 5, whole blood is withdrawn from a patient (step 30) through the inlet needle 70 and introduced into the first stage 12 of the separation chamber 14 of the fluid circuit 200, where the whole blood is subjected to a centrifugal field. The centrifugal field will separate an interface or MNC-containing layer from red blood cells, platelets, and plasma (step 32). As discussed above, the components such as red blood cells and platelets may be returned to the patient or may be diverted to a container for further processing, while the MNC-containing layer is collected for subsequent treatment.

Collection of MNCs may proceed in one or more cycles. The fluid collected in the MNC collection container 68 during each MNC collection cycle is referred to herein as a "pre-product," with the final MNC product eventually irradiated by the irradiation device 20 comprising the sum of all of the pre-products, along with any other additives present in the MNC collection container 68 at the time of irradiation (e.g., a diluting solution or photoactivation agent).

According to one aspect of the present disclosure, the irradiation device 20 is configured to treat an MNC product with a fixed dose of light that is selected for an MNC product having a predetermined volume and a predetermined hematocrit. In an exemplary embodiment, the predetermined volume is approximately 200 mL and the predetermined hematocrit is approximately 2%, but the predetermined volume and/or the predetermined hematocrit may vary without departing from the scope of the present disclosure. It should be understood that, when applying a fixed dose of light to the MNC product, the volume and the hematocrit of the MNC product must correspond to the predetermined volume and predetermined hematocrit (regardless of the number of MNC collection cycles executed by the separation device 10), otherwise the MNCs may not be properly irradiated. Thus, one aspect of the present disclosure is related to control of the separation device 10 so as to ensure that the MNC product has the proper volume and hematocrit, regardless of the number of MNC collection cycles executed by the separation device 10.

The number of MNC collection cycles executed in a given therapeutic procedure may depend upon any of a number of factors. For example, in one embodiment, the controller is programmed or configured to allow an operator to input the volume of blood to be processed during the procedure. Below a first volume (e.g., 3000 mL), the controller will determined that it is appropriate to execute one MNC collection cycle. Between the first volume and another, higher volume (e.g., 6000 mL), the controller will determine that it is appropriate to execute two MNC collection cycles. Above the higher second volume (optionally with an upper limit, such as 9000 mL), the controller will determine that it is appropriate to execute three MNC collection cycles. While only between one and three MNC collection cycles are executed in this example, it should be understood that the principles described herein may be employed in systems and methods in which more than three MNC collections cycles are executed in a single online ECP procedure.

In another embodiment, the controller is programmed or configured to allow an operator to input the target yield of MNCs to be collected and treated, which may also require the entry of a patient MNC pre-count (unless the yield of MNCs collected can be determined by the system during an ECP procedure). Based on the target MNC yield and the number of MNCs collected during each MNC collection cycle, the controller may determine the number of MNC collection cycles to execute. For example, if the target yield is $5 \times 10^9$ MNCs and the separation device 10 is predicted to collect $1 \times 10^9$ MNCs per MNC collection cycle, then the controller will determine that it is appropriate to execute the MNC collection cycle five times.

Effective treatment of the MNCs with light may require that the MNC product has a suitable hematocrit. In one embodiment, the separation device 10 includes a hematocrit sensor configured to monitor the hematocrit of any fluid conveyed toward the MNC collection container 68. The system controller may determine the RBC content of the MNC collection container 68 by multiplying the volumetric flow rate of the fluid by the hematocrit and control operation of the separation device 10 to arrive at the proper RBC content before the MNC product is irradiated by the irradiation device 20. In an exemplary embodiment, in which the predetermined volume of an MNC product is 200 mL and the predetermined hematocrit is 2%, the controller may control operation of the separation device 10 such that, over the course of the procedure (and regardless of the number of MNC collection cycles executed), approximately 4 mL of red blood cells are conveyed into the MNC collection container 68 as part of the MNC product. This will typically include diluting the contents of the MNC collection container 68 with a diluting solution such as plasma or saline (as shown in step 33) to arrive at the predetermined volume (200 mL in the exemplary embodiment) and predetermined hematocrit (2% in the exemplary embodiment).

In other embodiments, a hematocrit sensor may not be available, so other measures must be taken to ensure that the MNC product has the proper volume and hematocrit. For example, in the illustrated embodiment, the separation device 10 omits a hematocrit sensor capable of directly monitoring the hematocrit of the fluid conveyed toward the MNC collection container 68. In this case, a different approach is followed to arrive at an MNC product having a suitable volume and hematocrit. More specifically, the separation device 10 is provided with an optical sensor assembly 84 configured to monitor an outlet line defining a portion of the flow path between an outlet port of the first stage 12 of the separation chamber 14 and the MNC collection container 68. In the illustrated embodiment of FIG. 4, the optical sensor assembly 84 is configured to monitor an outlet line 86 positioned upstream of the right cassette 23R. However, in other embodiments, an optical sensor assembly may be configured to monitor some other outlet line of the flow path between the outlet port of the first stage 12 of the separation chamber 14 and the and the MNC collection container 68, such as the MNC line 80. In one embodiment, the optical sensor assembly 84 corresponds to the optical sensor described in U.S. Pat. No. 6,027,657, but the configuration of the optical sensor assembly 84 may vary without departing from the scope of the present disclosure, provided that it is capable of detecting the presence of the MNC-containing layer in the associated outlet line.

In an exemplary procedure, which may be executed by the illustrated separation device 10, separation and collection of the MNC-containing layer begins with blood being drawn into the first stage 12 of the separation chamber 14. The blood in the separation chamber 14 is separated into a plasma constituent (i.e., a low density component, which may include platelets), the interface or buffy coat or MNC-containing layer (i.e., an intermediate density component, which includes MNCs and may also include smaller red blood cells), and packed red blood cells (i.e., a high density component) by operation of the centrifuge of the separation device 10. Portions of the plasma constituent and packed red blood cells are removed from the first stage 12 via separate outlet ports, while the MNC-containing layer builds up in the first stage 12. The portions of the separated plasma constituent and packed red blood cells removed from the separation chamber 14 may be returned to the blood source and/or separately collected in collection containers, with a portion of the removed red blood cells being recirculated through the first stage 12 to move the interface into the proper position within the first stage 12.

When the interface has been established in the proper position within the first stage 12, blood draw and separation continue, with the volume of the MNC-containing layer building up within the first stage 12 while portions of the plasma constituent and red blood cells continue to be removed from the separation chamber 14. At least a portion of the separated red blood cells is collected in the RBC collection container 67 for later use.

To collect the MNC-containing layer, fluid flow through the outlet port used to remove the separated red blood cells from the first stage 12 is prevented, leaving only the plasma outlet port open for the removal of fluid from the first stage 12. At least a portion of the collected red blood cells is conveyed from the RBC collection container 67 into the first stage 12, which forces the MNC-containing layer to exit the first stage 12 via the plasma outlet port. The plasma constituent present in the first stage 12 during this phase will exit via the plasma outlet port in advance of the MNC-containing layer. The optical sensor assembly 84 monitors the fluid exiting the first stage 12 to detect the presence of the MNC-containing layer, which (in one embodiment) corresponds to an increase in the optical density of the fluid passing through the outlet line 86. The plasma constituent may be conveyed into the MNC collection container 68 as part of the pre-product or may be directed elsewhere, such as being returned to the blood source.

Once the MNC-containing layer has been conveyed out of the separation chamber 14, the separated red blood cells will begin exiting the first stage 12 via the plasma outlet port, behind the MNC-containing layer. At least a portion of the red blood cells exiting the separation chamber 14 during this phase may be directed into the MNC collection container 68 to increase the hematocrit of the fluid within the MNC collection container 68, while another portion of the red blood cells may be directed elsewhere (e.g., being returned to the blood source), if not needed to increase the hematocrit of the fluid within the MNC collection container 68.

The same volume of MNCs may be collected as a part of each pre-product, such that the system controller will know the amount of red blood cells conveyed into the MNC collection container 68 if a selected volume of the contents of the separation chamber 14 (referred to herein as an "RBC offset") is conveyed out of the separation chamber 14 after the optical sensor assembly 84 has detected the MNC-containing layer. For example, if the separation device collects 3 mL of MNCs during each MNC collection phase and the RBC offset is selected to be 5 mL, then the controller will know that the first 3 mL of fluid flowing past the optical sensor assembly 84 will be the MNC-containing layer, while the next 2 mL of fluid flowing past the optical sensor assembly 84 will be packed red blood cells. It should be understood that the RBC offset is not necessarily equal to the volume of the pre-product collected during a particular cycle, depending on the location of the optical sensor assembly 84. For example, if the volume of the flow path between the optical sensor assembly 84 and the MNC collection container 68 is 1.5 mL and the RBC offset is 5 mL (with 3 mL of MNCs collected during each cycle), then the pre-product will comprise 3 mL of MNCs and 0.5 mL of red blood cells, with 1.5 mL of red blood cells remaining in the flow path between the optical sensor assembly 84 and the MNC collection container 68.

The controller may use this information to control the RBC content of each pre-product. For example, if the controller has determined that only one MNC collection cycle is to be executed, then it may operate the separation device 10 with an RBC offset sufficient to provide the entire required volume of red blood cells to the MNC collection container 68 (which may be approximately 6.8 mL in one embodiment). If the controller has determined that two MNC collection cycles are to be executed, then it may operate the separation device 10 with a smaller RBC offset (compared to a single-cycle procedure, which may be approximately 6.0 mL in one embodiment) to provide half of the required volume of red blood cells to the MNC collection container 68 during each MNC collection cycle. If the controller has determined that three MNC collection cycles are to be executed, then it may operate the separation device 10 with an even smaller RBC offset (compared to a single- or double-cycle procedure, which may be approximately 5.2 mL in one embodiment) to provide one-third of the required volume of red blood cells to the MNC collection container 68 during each MNC collection cycle. Alternatively, rather than using the same RBC offset in each MNC collection cycle of a multi-cycle procedure, it is also within the scope of the present disclosure for the RBC offset of at least two MNC collection cycles of a single procedure to be different. For example, an earlier cycle may employ a smaller RBC offset than a later cycle or a larger RBC offset than a later cycle. Thus, regardless of how many MNC collection cycles are executed and the number of pre-products combined to produce the MNC product, it is ensured that the MNC product will have the proper RBC content and (following dilution, as necessary) volume.

Regardless of how exactly the controller directs the operation of the separation device 10 to provide the fluid in the MNC collection container 68 with the proper RBC content and volume, the contents of the MNC collection container 68 are then combined with 8-MOP or any other suitable photoactivation agent, such as a psoralen compound (step 34). Alternatively, the MNC collection container 68 may be initially filled with the desired volume of the agent. In one example, the separation device 10, under the direction of its controller, may be programmed or configured to automatically deliver the desired amount of photoactive agent from, for example, container 69 before or after MNC collection, based on the volume of MNCs collected or to be collected. The photoactivation agent is combined with the collected and diluted MNCs to arrive at a mixture (referred to herein as the MNC product) having the proper composition for irradiation. When 8-MOP is used, the MNCs may be combined with the 8-MOP to arrive at a final 8-MOP concentration of about 330 nanograms/mL or in a range of about 100 to 500 nanograms/mL.

As noted above, the MNCs may be irradiated in the MNC collection container 68, in which case the MNC collection container 68 is configured so as to be suitable for irradiation by light of a selected wavelength. By "suitable," it is meant that the walls of the MNC collection container 68 are sufficiently transparent to light of the selected wavelength to activate the photoactive agent. In treatments using UVA light, for example, container walls made of ethylene vinyl acetate are suitable. The MNC collection container 68 may placed inside the irradiation device 20 by the operator or, more preferably, may be placed inside an irradiation chamber of the irradiation device 20 at the beginning of the ECP procedure and prior to whole blood withdrawal (as shown by the broken lines representing device 20 in FIG. 4). In any event, the MNC collection container 68 preferably remains integrally connected to the remainder of the fluid circuit 200 during the entire procedure, thereby maintaining the closed or functionally closed condition of the fluid circuit 200.

The mixture of MNCs and photoactivation agent is then irradiated for a selected period of time (step 36), which may be a fixed dose of light according to an aspect of the present disclosure. In one non-limiting example, during treatment, the MNC product may be exposed to UV bulbs having a wavelength in the UVA range of about 320 nm to 400 nm for a selected period of time, such as approximately 10-60 minutes, resulting in an average UVA exposure of approximately 0.5-5.0 J/cm$^2$ or approximately 1-2 J/cm$^2$ or approximately 1.5 J/cm$^2$ per lymphocyte.

Once treatment is complete, the treated MNCs may be returned to the separation device 10, such as to the first stage 12 of the separation chamber 14 in the centrifuge of the separation device 10 (step 38). For example, one of the pumps of the separation device 10 associated with the right cassette 23R may be actuated by the controller to withdraw the treated MNCs from the MNC collection container 68, through the right cassette 23R, and back into the first stage 12 of the separation chamber 14. Once inside separation chamber 14, the MNCs may be concentrated (step 40) by centrifugation to remove the supernatant from the treated MNCs (step 41), with the supernatant being conveyed to the waste container 62.

Concentrating treated MNCs prior to reinfusion allows for the concentrated MNCs to have a smaller total volume than MNCs that have not been concentrated, allowing for a smaller volume of concentrated MNCs to be more quickly reinfused to the patient. The concentrated MNCs may be resuspended in a suitable resuspension medium (e.g., plasma, saline), as shown in step 43, and returned to the patient.

Optionally, prior to return to the patient, the concentrated and treated MNCs may be combined with a suitable wash solution (step 42). If the concentrated MNCs are combined with wash solution, the mixture is subjected to a centrifugal field within the separation chamber 14, which separates the MNCs from any remaining supernatant (step 44). In particular, any remaining unbound and excess photoactive agent will be separated from the concentrated MNCs and suspended in the supernatant. The supernatant may then be withdrawn to the waste container 62, while the concentrated and washed MNCs may be resuspended with a resuspension solution (such as, but not limited to, plasma or saline) as shown in step 45, and returned to the patient, as shown in step 46.

It should be understood that the steps described above are preferably performed with the patient connected to the system, such that the entire treatment, including the washing of the treated MNCs, is deemed to be an online procedure. Thus, in accordance with the systems and methods described herein, a multifunctional separation device 10, a disposable fluid circuit 200, and a separate irradiation device 20 may be used to perform an online ECP procedure. As previously mentioned, the online nature of the approach described herein avoids the necessity for additional MNC product labeling or handling, as the MNCs never leave the fluid circuit 200 and the MNC collection container 68 is never disconnected from the fluid circuit 200 during the entire procedure. In other words, the fluid circuit 200 provides a sterile, closed pathway between the multifunctional separation device 10 and the irradiation device 20 such that from the time MNCs are harvested from the patient to the time that the treated MNCs are reinfused to the patient, an online closed system is maintained and reinfusion to the correct patient is ensured.

Aspects

Aspect 1. An extracorporeal photopheresis system, comprising: a separation device configured to execute a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product, and produce a single mononuclear cell product from said pre-product; an irradiation device configured to irradiate the mononuclear cell product using a fixed dose of light; and a controller configured to control operation of at least the separation device, wherein the controller is further configured to allow for execution of one or more of the mononuclear cell collection cycles prior to production of the single mononuclear cell product, with the single mononuclear cell product being produced using the pre-products collected during each mononuclear cell collection cycle, and control the separation device to produce the mononuclear cell product with a predetermined volume and a predetermined hematocrit, regardless of the number of mononuclear cell collection cycles executed and the number of pre-products used to produce the mononuclear cell product.

Aspect 2. The extracorporeal photopheresis system of Aspect 1, further comprising a fluid processing assembly, wherein the mononuclear cell collection cycle comprises drawing blood into the fluid processing assembly from a blood source, conveying the blood into a separation chamber of the fluid processing assembly, separating the blood in the separation chamber into the plasma constituent, the mononuclear cell-containing layer, and the red blood cells, conveying at least a portion of the separated red blood cells from the separation chamber to a red blood cell collection container of the fluid processing assembly while allowing a volume of the mononuclear cell-containing layer to increase in the separation chamber, conveying at least a portion of the contents of the red blood cell collection container to the separation chamber to convey at least a portion of the contents of the separation chamber, including the mononuclear cell-containing layer, out of the separation chamber via an outlet line of the fluid processing assembly toward a mononuclear cell collection container of the fluid processing assembly, detecting the mononuclear cell-containing layer in the outlet line, and conveying a selected volume of the contents of the separation chamber out of the separation chamber via the outlet line after detecting the mononuclear-cell containing layer in the outlet line, with the fluid conveyed from the separation chamber into the mononuclear cell collection container during each mononuclear cell collection cycle comprising the pre-product collected during that mononuclear cell collection cycle.

Aspect 3. The extracorporeal photopheresis system of Aspect 2, wherein the controller is configured such that the selected volume decreases as the number of times that the mononuclear cell collection cycle is executed increases.

Aspect 4. The extracorporeal photopheresis system of any one of Aspects 2-3, wherein the controller is configured such that, when the mononuclear cell collection cycle is executed at least two times, the selected volume is the same for each mononuclear cell collection cycle.

Aspect 5. The extracorporeal photopheresis system of any one of Aspects 2-3, wherein the controller is configured such that, when the mononuclear cell collection cycle is executed at least two times, the selected volume is different for at least two of the mononuclear cell collection cycles.

Aspect 6. The extracorporeal photopheresis system of Aspect 5, wherein the controller is configured such that the selected volume is lower for at least one of the mononuclear cell collection cycles than for a subsequent mononuclear cell collection cycle.

Aspect 7. The extracorporeal photopheresis system of Aspect 5, wherein the controller is configured such that the selected volume is greater for at least one of the mononuclear cell collection cycles than for a subsequent mononuclear cell collection cycle.

Aspect 8. The extracorporeal photopheresis system of any one of Aspects 2-7, wherein the controller is further configured to allow for the selection of a total volume of blood to be drawn into the fluid processing assembly from the blood source, and the number of times that the mononuclear cell collection cycle is executed is based at least in part on the total volume of blood to be drawn into the fluid processing assembly from the blood source.

Aspect 9. The extracorporeal photopheresis system of any one of Aspects 2-7, wherein the controller is further configured to allow for the selection of a target yield of mononuclear cells to be collected, and the number of times that the mononuclear cell collection cycle is executed is based at least in part on the target yield of mononuclear cells to be collected and a mononuclear cell pre-count of the blood source.

Aspect 10. The extracorporeal photopheresis system of any one of the preceding Aspects, wherein the predetermined volume is approximately 200 mL and the predetermined hematocrit is approximately 2%.

Aspect 11. A method for extracorporeal photopheresis, comprising: executing a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product; optionally repeating the mononuclear cell collection cycle; producing a single mononuclear cell product using the pre-products collected during each mononuclear cell collection cycle; irradiating the mononuclear cell product using a fixed dose of light; and returning at least a portion of the irradiated mononuclear cell product to the blood source, wherein the mononuclear cell product has a predetermined volume and a predetermined hematocrit regardless of the number of mononuclear cell collection cycles executed and the number of pre-products used to produce the mononuclear cell product.

Aspect 12. The method of Aspect 11, wherein said executing the mononuclear cell collection cycle comprises drawing blood into a fluid processing assembly from a blood source, conveying the blood into a separation chamber of the fluid processing assembly, separating the blood in the separation chamber into the plasma constituent, the mononuclear cell-containing layer, and the red blood cells, conveying at least a portion of the separated red blood cells from the separation chamber to a red blood cell collection container while allowing a volume of the mononuclear cell-containing layer to increase in the separation chamber, conveying at least a portion of the contents of the red blood cell collection container to the separation chamber to convey at least a portion of the contents of the separation chamber, including the mononuclear cell-containing layer, out of the separation chamber via an outlet line toward a mononuclear cell collection container, detecting the mononuclear cell-containing layer in the outlet line, and conveying a selected volume of the contents of the separation chamber out of the separation chamber via the outlet line after detecting the mononuclear-cell containing layer in the outlet line, said producing a single mononuclear cell product includes increasing the volume of the contents of the mononuclear cell collection container to the predetermined volume having the predetermined hematocrit, and the selected volume is based at least in part on the number of times that the mononuclear cell collection cycle is executed.

Aspect 13. The method of Aspect 12, wherein the selected volume decreases as the number of times that the mononuclear cell collection cycle is executed increases.

Aspect 14. The method of any one of Aspects 12-13, wherein the mononuclear cell collection cycle is repeated at least one time, and the selected volume is the same for each mononuclear cell collection cycle.

Aspect 15. The method of any one of Aspects 12-13, wherein the mononuclear cell collection cycle is repeated at least one time, and the selected volume is different for at least two of the mononuclear cell collection cycles.

Aspect 16. The method of Aspect 15, wherein the selected volume is lower for at least one of the mononuclear cell collection cycles than for a subsequent mononuclear cell collection cycle.

Aspect 17. The method of Aspect 15, wherein the selected volume is greater for at least one of the mononuclear cell collection cycles than for a subsequent mononuclear cell collection cycle.

Aspect 18. The method of any one of Aspects 12-17, further comprising selecting a total volume of blood to be drawn into the fluid processing assembly from the blood source, wherein the number of times that the mononuclear cell collection cycle is repeated is based at least in part on the total volume of blood to be drawn into the fluid processing assembly from the blood source.

Aspect 19. The method of any one of Aspects 12-17, further comprising selecting a target yield of mononuclear cells to be collected, wherein the number of times that the mononuclear cell collection cycle is repeated is based at least in part on the target yield of mononuclear cells to be collected and a mononuclear cell pre-count of the blood source.

Aspect 20. The method of any one of Aspects 12-19, wherein the predetermined volume is approximately 200 mL and the predetermined hematocrit is approximately 2%.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An extracorporeal photopheresis system, comprising:
a separation device configured to
execute a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product, and
produce a single mononuclear cell product from said pre-product;
an irradiation device configured to irradiate the mononuclear cell product using a fixed dose of light; and
a controller configured to control operation of at least the separation device, wherein the controller is further configured to allow for execution of one or more of the mononuclear cell collection cycles prior to production of the single mononuclear cell product, with the single mononuclear cell product being produced using the pre-products collected during each mononuclear cell collection cycle, and control the separation device to produce the mononuclear cell product with a predetermined volume and a predetermined hematocrit, regardless of the number of mononuclear cell collection cycles executed and the number of pre-products used to produce the mononuclear cell product.

2. The extracorporeal photopheresis system of claim 1, further comprising a fluid processing assembly, wherein the mononuclear cell collection cycle comprises drawing blood into the fluid processing assembly from a blood source, conveying the blood into a separation chamber of the fluid processing assembly, separating the blood in the separation chamber into the plasma constituent, the mononuclear cell-containing layer, and the red blood cells, conveying at least a portion of the separated red blood cells from the separation chamber to a red blood cell collection container of the fluid processing assembly while allowing a volume of the mononuclear cell-containing layer to increase in the separation chamber, conveying at least a portion of the contents of the red blood cell collection container to the separation chamber to convey at least a portion of the contents of the separation chamber, including the mononuclear cell-containing layer, out of the separation chamber via an outlet line of the fluid processing assembly toward a mononuclear cell collection container of the fluid processing assembly, detecting the mononuclear cell-containing layer in the outlet line, and conveying a selected volume of the contents of the separation chamber out of the separation chamber via the outlet line after detecting the mononuclear-cell containing layer in the outlet line, with the fluid conveyed from the separation chamber into the mononuclear cell collection container during each mononuclear cell collection cycle comprising the pre-product collected during that mononuclear cell collection cycle.

3. The extracorporeal photopheresis system of claim 2, wherein the controller is configured such that the selected volume decreases as the number of times that the mononuclear cell collection cycle is executed increases.

4. The extracorporeal photopheresis system of claim 2, wherein the controller is configured such that, when the mononuclear cell collection cycle is executed at least two times, the selected volume is the same for each mononuclear cell collection cycle.

5. The extracorporeal photopheresis system of claim 2, wherein the controller is configured such that, when the mononuclear cell collection cycle is executed at least two times, the selected volume is different for at least two of the mononuclear cell collection cycles.

6. The extracorporeal photopheresis system of claim 5, wherein the controller is configured such that the selected volume is lower for at least one of the mononuclear cell collection cycles than for a subsequent mononuclear cell collection cycle.

7. The extracorporeal photopheresis system of claim 5, wherein the controller is configured such that the selected volume is greater for at least one of the mononuclear cell collection cycles than for a subsequent mononuclear cell collection cycle.

8. The extracorporeal photopheresis system of claim 2, wherein the controller is further configured to allow for the selection of a total volume of blood to be drawn into the fluid processing assembly from the blood source, and the number of times that the mononuclear cell collection cycle is executed is based at least in part on the total volume of blood to be drawn into the fluid processing assembly from the blood source.

9. The extracorporeal photopheresis system of claim 2, wherein the controller is further configured to allow for the selection of a target yield of mononuclear cells to be collected, and the number of times that the mononuclear cell collection cycle is executed is based at least in part on the target yield of mononuclear cells to be collected and a mononuclear cell pre-count of the blood source.

10. The extracorporeal photopheresis system of claim 1, wherein the predetermined volume is approximately 200 mL and the predetermined hematocrit is approximately 2%.

11. A method for extracorporeal photopheresis, comprising:

executing a mononuclear cell collection cycle in which blood is separated into a plasma constituent, a mononuclear cell-containing layer, and red blood cells, with at least a portion of the mononuclear cell-containing layer and at least a portion of the separated red blood cells being collected together as a pre-product;

optionally repeating the mononuclear cell collection cycle;

producing a single mononuclear cell product using the pre-products collected during each mononuclear cell collection cycle;

irradiating the mononuclear cell product using a fixed dose of light; and returning at least a portion of the irradiated mononuclear cell product to the blood source, wherein the mononuclear cell product has a predetermined volume and a predetermined hematocrit regardless of the number of mononuclear cell collection cycles executed and the number of pre-products used to produce the mononuclear cell product.

12. The method of claim 11, wherein said executing the mononuclear cell collection cycle comprises drawing blood into a fluid processing assembly from a blood source, conveying the blood into a separation chamber of the fluid processing assembly, separating the blood in the separation chamber into the plasma constituent, the mononuclear cell-containing layer, and the red blood cells, conveying at least a portion of the separated red blood cells from the separation chamber to a red blood cell collection container while allowing a volume of the mononuclear cell-containing layer to increase in the separation chamber, conveying at least a portion of the contents of the red blood cell collection container to the separation chamber to convey at least a portion of the contents of the separation chamber, including the mononuclear cell-containing layer, out of the separation chamber via an outlet line toward a mononuclear cell collection container, detecting the mononuclear cell-containing layer in the outlet line, and conveying a selected volume of the contents of the separation chamber out of the separation chamber via the outlet line after detecting the mononuclear-cell containing layer in the outlet line, said producing a single mononuclear cell product includes increasing the volume of the contents of the mononuclear cell collection container to the predetermined volume having the predetermined hematocrit, and the selected volume is based at least in part on the number of times that the mononuclear cell collection cycle is executed.

13. The method of claim 12, wherein the selected volume decreases as the number of times that the mononuclear cell collection cycle is executed increases.

14. The method of claim 12, wherein the mononuclear cell collection cycle is repeated at least one time, and the selected volume is the same for each mononuclear cell collection cycle.

15. The method of claim 12, wherein the mononuclear cell collection cycle is repeated at least one time, and the selected volume is different for at least two of the mononuclear cell collection cycles.

16. The method of claim 15, wherein the selected volume is lower for at least one of the mononuclear cell collection cycles than for a subsequent mononuclear cell collection cycle.

17. The method of claim 15, wherein the selected volume is greater for at least one of the mononuclear cell collection cycles than for a subsequent mononuclear cell collection cycle.

18. The method of claim 12, further comprising selecting a total volume of blood to be drawn into the fluid processing assembly from the blood source, wherein the number of times that the mononuclear cell collection cycle is repeated is based at least in part on the total volume of blood to be drawn into the fluid processing assembly from the blood source.

19. The method of claim 12, further comprising selecting a target yield of mononuclear cells to be collected, wherein the number of times that the mononuclear cell collection cycle is repeated is based at least in part on the target yield of mononuclear cells to be collected and a mononuclear cell pre-count of the blood source.

20. The method of claim 12, wherein the predetermined volume is approximately 200 mL and the predetermined hematocrit is approximately 2%.

* * * * *